United States Patent [19]

Smith et al.

[11] Patent Number: 5,519,319

[45] Date of Patent: May 21, 1996

[54] OBTAINING MEASUREMENTS OF IMPROVED ACCURACY OF ONE OR MORE POLYMER PROPERTIES WITH AN ON-LINE NMR SYSTEM

[75] Inventors: Thomas B. Smith, Atkinson; Scott A. Marino, Windham, both of N.H.; Ronald J. Tache, Malden, Mass.; David R. Day, Boxford, Mass.; Christian I. Tanzer, Bedford, Mass.; Tadd B. Hughes, Winchester, Mass.; Ajoy K. Roy, Danvers, Mass.

[73] Assignee: Auburn International, Inc., Danvers, Mass.

[21] Appl. No.: 491,632

[22] Filed: Jun. 19, 1995

Related U.S. Application Data

[63] Continuation-in-part of Ser. No. 370,862, Jan. 10, 1995, and Ser. No. 371,091, Jan. 10, 1995, which is a continuation-in-part of Ser. No. 226,024, Apr. 11, 1994, abandoned, which is a continuation of Ser. No. 885,633, May 19, 1992, Pat. No. 5,302,897, said Ser. No. 370,862, is a continuation-in-part of Ser. No. 226,061, Apr. 11, 1994, abandoned, which is a continuation of Ser. No. 794,931, Nov. 20, 1991, Pat. No. 5,302,896.

[51] Int. Cl.$^6$ ................................................. G01V 03/00
[52] U.S. Cl. ........................... 324/306; 324/307; 324/309
[58] Field of Search .................................... 324/300, 306, 324/307, 309

[56] References Cited

U.S. PATENT DOCUMENTS

| | | | |
|---|---|---|---|
| 5,015,954 | 5/1991 | Dechene et al. | 324/307 |
| 5,049,819 | 9/1991 | Dechene et al. | 324/307 |
| 5,302,896 | 4/1994 | Dechene et al. | 324/307 |
| 5,302,897 | 4/1994 | Tache et al. | 324/307 |
| 5,319,308 | 6/1994 | Dechene et al. | 324/307 |
| 5,367,260 | 11/1994 | Dechene et al. | 324/307 |
| 5,397,987 | 3/1995 | Garritano | 324/307 |
| 5,408,181 | 4/1995 | Dechene et al. | 324/307 |

*Primary Examiner*—Sandra L. O'Shea
*Assistant Examiner*—Mack Haynes
*Attorney, Agent, or Firm*—Testa, Hurwitz & Thibeault

[57] ABSTRACT

A nuclear magnetic resonance (NMR) system, and related method, develops two or more regression equations or models for a particular polymer property of interest (e.g., melt index or MI) during a calibration procedure using known samples of a material. The polymer material can be, for example, a plastic (e.g., polyethylene, polypropylene, or polystyrene) or a rubber (e.g., ethylene propylene rubber). Regression models for one or more discrete (i.e., two-valued) variables also are developed during calibration, and these models allow a prediction to be made about which of the two or more property (e.g., MI) models should be used for any particular sample of unknown material. The prediction obtained from the discrete variable model indicates which of the two or more models will produce the most accurate estimation of the property of interest for the unknown sample. The best model is thus selected, and then it is used to estimate the property of interest.

12 Claims, 12 Drawing Sheets

OBTAINING MEASUREMENTS OF IMPROVED ACCURACY OF ONE OR MORE POLYMER PROPERTIES WITH AN ON-LINE NMR SYSTEM

CROSS-REFERENCE TO RELATED PATENTS AND APPLICATIONS

This application is a continuation-in-part of the following two pending U.S. patent applications: (1) U.S. patent application Ser. No. 08/370,862 filed on Jan. 10, 1995 which is a continuation-in-part of U.S. patent application Ser. No. 08/226,061 filed on Apr. 11, 1994 (now abandoned) which is a continuation of U.S. patent application Ser. No. 794,931 filed on Nov. 20, 1991, now U.S. Pat. No. 5,302,896 issued to Dechene et al. on Apr. 12, 1994; and (2) U.S. patent application Ser. No. 08/371,091 filed on Jan. 10, 1995 which is a continuation-in-part of U.S. patent application Ser. No. 08/226,024 filed on Apr. 11, 1994 (now abandoned) which is a continuation of U.S. patent application Ser. No. 885,633 filed on May 19, 1992, now U.S. Pat. No. 5,302,897 issued to Dechene et al. on Apr. 12, 1994.

Also, this application is related to the following U.S. patents: U.S. Pat. No. 5,015,954 issued to Dechene et al. on May 14, 1991; U.S. Pat. No. 5,049,819 issued to Dechene et al. on Sep. 17, 1991; U.S. Pat. No. 5,319,308 issued to Dechene et al. on Jun. 7, 1994; U.S. Pat. No. 5,367,260 issued to Dechene et al. on Nov. 22, 1994; and U.S. Pat. No. 5,408,181 issued to Dechene et al. on Apr. 18, 1995.

Each of these U.S. patents and patent applications is of common assignment with this application, and the disclosures of all of the above-listed patents and patent applications are incorporated herein by reference.

FIELD OF THE INVENTION

The present invention involves using pulsed nuclear magnetic resonance (NMR) techniques to measure physical properties (e.g., xylene solubles, density, rubber/oil content, and flow rates such as melt index, flow rate ratio, melt flow) of polymer materials (e.g., rubber and plastics such as polypropylene, polyethylene, and polystyrene).

BACKGROUND OF THE INVENTION

The pulsed NMR techniques described herein, and in the above-identified related patents and applications, involve the use of a pulsed burst or pulse of energy designed to excite the nuclei of a particular nuclear species of a sample being measured. The protons, or the like, of the sample are first precessed in an essentially static magnetic field. The precession thus is modified by the pulse. After the application of the pulse, there occurs a free induction decay (FID) of the magnetization associated with the excited nuclei. That is, the transverse magnetization associated with the excited nuclei relaxes back to its equilibrium value of zero, and this relaxation produces a changing magnetic field which is measured in adjacent pickup coils. A representation of this relaxation is the FID waveform or curve.

An NMR system described herein, and in the above-identified related patents and applications, takes measurements of physical properties of polymer materials (e.g., rubber, plastics, etc.) and relates those properties back to, for example, flow rates (e.g., melt index), crystallinity, composition, density, and tacticity by performing the following analysis methods. The NMR system is first calibrated with known samples by determining the physical types, properties, and quantities of the target nuclei in each known sample. Unknown samples are then introduced into the NMR system, and the system determines the physical types, properties, and quantities of the target nuclei in each unknown sample based on the calibration information.

The analysis methods performed by the NMR system involve decomposing an FID curve associated with a known sample into a sum of separate time function equations. Useful time function equations include Gaussians, exponentials, Abragams (defined herein as Gaussian multiplied by the quantity $sin(\omega t)$ divided by $\omega t$), modified exponential (defined herein as $Ce^{-z}$ where C is a constant, $z=(kt)^\alpha$, and $\alpha$ lies between 0 and 1 or 1 and 2), modified Gaussian (defined herein as Gaussian multiplied by the cosine of the square root of t), and trigonometric.

The coefficients of the time function equations are derived from the FID by use of a Marquardt-Levenberg (M-L) iterative approximation that minimizes the Chi-Squared function. This iterative technique is well-known in the art. Other known-in-the-art iterative techniques can be used instead of M-L including a Gauss-Jordan technique, a Newton-Raphson technique, and/or a "steepest descent" technique.

From the time functions, a set of parameters is calculated. Some of these parameters are ratios of the y-axis intercepts, decay times (or time constants of decay) for each of the time functions, and the cross products and reciprocals thereof. The sample temperature may form the basis for another parameter.

Statistical modeling techniques are then used to select a subset of these parameters to form a regression equation or model. Regression coefficients are then computed for this parameter subset. These regression coefficients represent the regression model which relates the parameter subset to the types, properties, and quantities of the target nuclei in the known sample.

After the NMR system has been calibrated with one or more known samples, unknown samples can be introduced thereinto.

When an unknown sample is introduced into the calibrated NMR system, the FID associated with the unknown sample is decomposed into a sum of separate time function equations. The coefficients of the time function equations are derived from the FID by use of the iterative M-L technique. From the time functions, parameters are calculated. The parameters are then "regressed" via the regression model to yield the types, properties, and quantities of the target nuclei in the unknown sample. That is, the measured parameters from the FID of the unknown sample are used with the regression model, and the types, properties, and quantities of the target nuclei in the unknown sample are determined. This information is related to a property of the sample-under-test such as density, xylene solubles, or flow rates (e.g., melt index, flow rate ratio, and/or melt flow).

It should be understood that the regression model is a multi-dimensional regression equation or model, and it may be linear or non-linear. Because it is multi-dimensional, it may not be graphically represented. As an example of a regression technique, consider that the grade point average of each of the students at a college were related to that student's SAT score and high school standing, forming a three dimensional space. The line formed is a "regression line" which may be graphed. A new student's grade point average may be predicted by placing the new student's SAT score and high school standing on the "regression line" and "reading" the grade point average.

Melt index (MI) has been defined for polyethylene as the flow rate obtained under condition 190/2.16 (note 19, ASTM, or American Society for Testing and Materials, No. D1238-90b). In general, MI is a measure of viscosity. Flow rate ratio (FRR) has been defined for polyethylene as a dimensionless number derived by dividing the flow rate at condition 190/10 by the flow rate at condition 190/2.16 (paragraph 8.3, page 396, ASTM No. D1238-90b). In some cases, the logarithm of FRR is used instead of FRR. Melt flow (MF) has been defined for polypropylene as the flow rate at condition 230/2.16 (ASTM No. D1238-90b).

For some polymer materials, the NMR system may produce unacceptable results. For example, for some polyethylene "grades" (i.e., polyethylene products having specified density and MI values), the standard deviation between the MI estimation obtained by the NMR system and the "actual" MI value (e.g., the MI value obtained by a manual laboratory ASTM method) can become unacceptable if the calibration is carried out over the entire product "slate" (i.e., the totality of product grades manufactured by a particular producer).

SUMMARY OF THE INVENTION

It has been found that the relationship of some polymer properties (e.g., MI or average molecular weight) with NMR parameters (or transforms) tends to be strongly non-linear over a broad product slate. It is desirable to divide a broad slate into smaller segments over which better linearity holds. Polymer property (e.g., MI) regressions are thus greatly facilitated. This has been found to be the case with, for example, smaller MI's (or higher molecular weights). Similarly, some polymer materials such as polyethylene with, for example, higher density (e.g., greater than 0.95) tend to be very rigid, whereas lower density (e.g., less than 0.92) grades are more mobile. In fact, it has been found that for acceptable MI calibration, polyethylene with a density less than or equal to about 0.92 may need to be treated separately from polyethylene of higher densities.

A regression model prepared from samples only in a narrow product grade range has been found to yield acceptable and improved results for some polymer property calibrations such as a melt index (MI) calibration.

It is an object of this invention to improve the accuracy of the estimations of polymer properties (e.g., MI) produced by an on-line nuclear magnetic resonance (NMR) system for various polymer materials. In one particular embodiment, the NMR system produces MI measurements having standard deviations less than 10%, and more preferably about 5–7% or less.

It is also an object of this invention to use a regression model to determine more accurately a property of interest (e.g., xylene solubles, density, rubber/oil content, or flow rates such as MI, FRR, and MF) of a plastic (e.g., polypropylene, polyethylene, or polystyrene) or any other polymer including rubber. The techniques according to the invention are for use "on-line" and do not require any external input, other than the unknown sample itself, in order to determine accurately the sample's property of interest. The appropriate regression model is selected automatically, without any operator or user input or interaction, from a plurality of different regression models associated with the particular property of interest.

The NMR system and method according to the invention develops two or more regression equations or models for a polymer property such as MI (e.g., $MI_1$, $MI_2$, and $MI_3$) during a calibration procedure using known samples.

Regression models for one or more discrete (i.e., two-valued) variables also are developed during calibration, and these models allow a prediction to be made about which of the plurality of MI regression models should be used for any particular unknown sample. If there are two regression models for the particular polymer property of interest, only a single discrete variable regression model is needed, and the two possible values of the variable correspond to the two property models. That is, in the case of two property models, the single discrete variable model yields a value (one of the two possible values) which corresponds to the property model that will produce the most accurate measurement of that property for an unknown sample. If there are N regression models for the property of interest and N is greater than two, N discrete variable regression models are used and each one corresponds to a different one of the N property models. In this case, the property model that corresponds to the discrete variable regression model yielding the largest value is selected as the property model that will produce the most accurate measurement of the property of interest for the unknown sample. In either case, after having selected one of the plurality of property regression models by using the discrete variable regression model(s), the selected property model is applied to data derived from the unknown sample to determine the property of interest (e.g., MI) of the unknown sample.

The discrete variable is created prior to model making based on, for example, laboratory density and MI data for polyethylene samples or laboratory solubles/tacticity and MF data for polypropylene. This data is gathered prior to model making from various sources such as users of NMR systems conforming to the descriptions in the above-listed related patents and applications. For example, the discrete variable can be a Boolean variable which has a certain value (e.g., 1) for polyethylene with a density $\leq 0.9225$ grams/milliliter and an $MI \leq 1.25$ and another value (e.g., 0) for any other density/MI grade polyethylene. It should be understood that more complex conditions might be applied such as density and/or MI within a certain range (e.g., 0.91<density<0.9225 and 0.2<MI<1.25). Using such a discrete variable or variables results in MI measurements being acceptable regardless whether an unknown sample is outside or inside of the density/MI range identified above. In one embodiment, an acceptable MI measurement has a standard deviation less than 10%, and preferably about 5–7% or less. If the sample is polyethylene falling within the range, a certain MI regression model is used. If the sample falls outside of the range, a different MI regression model is used. Regardless of the particular grade of the sample, the invention automatically selects the MI or other polymer property model which results in the most accurate measurement for that property.

In accordance with the invention, a plurality of regression models for a variety of polymer properties (e.g., MI, xylene solubles, density, rubber/oil content, FRR, or MF) can be developed during the calibration procedure. For example, two or more regression models for rubber content (e.g., $R_1$ and $R_2$) can be developed. In this case, the discrete Boolean variable regression model allows a prediction to be made about which of the two rubber content regression models should be used for any particular unknown sample. After the rubber content model is selected by using the discrete variable model, the selected rubber content regression model is applied to data derived from the unknown sample to determine the rubber content of the unknown sample.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1A:
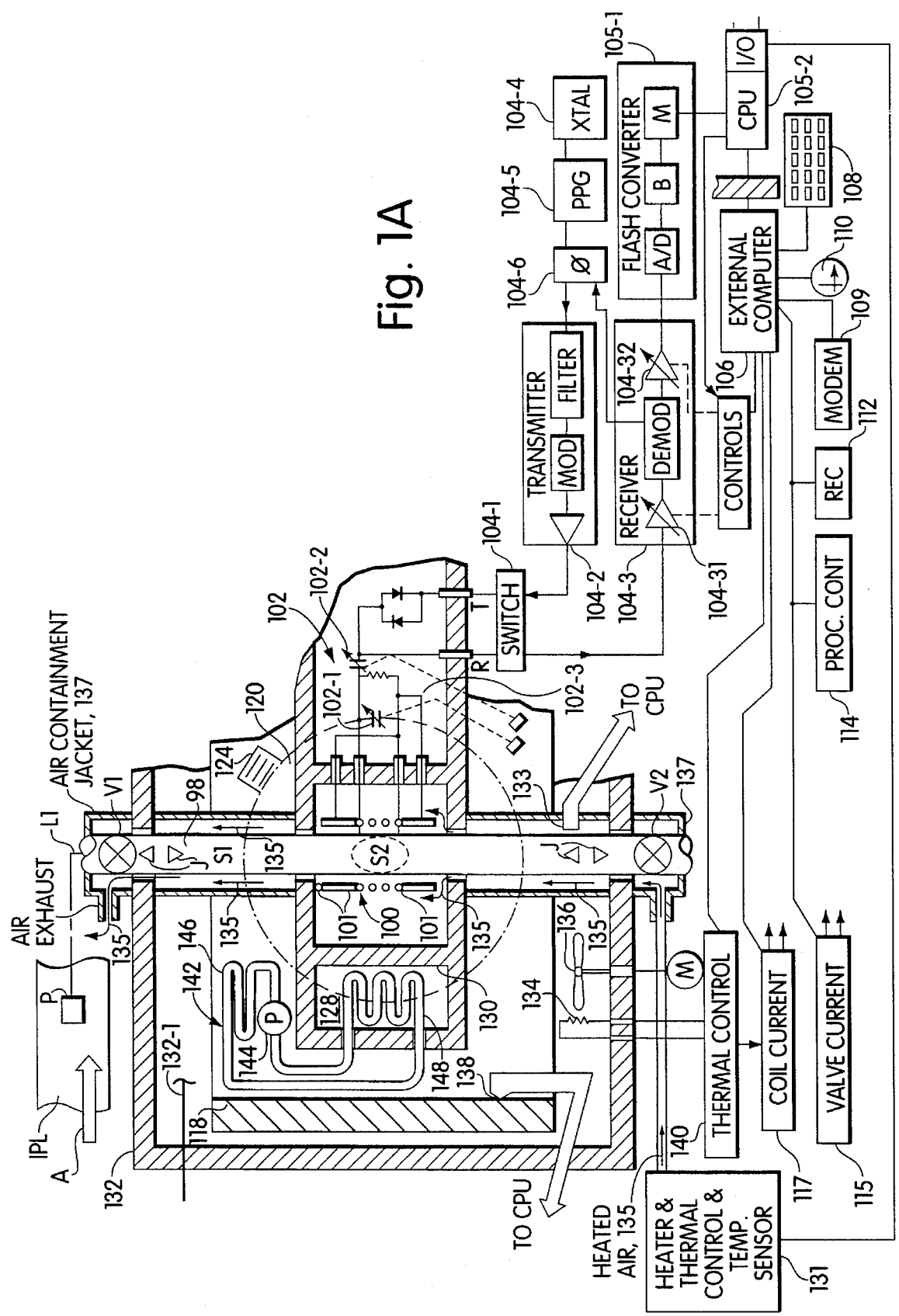
FIGS. 1A, 1B and 1C are block/schematic diagrams of a preferred embodiment of a pulsed NMR system according to the invention which is suitable for measuring various properties of a range of polymer materials.

FIG. 1A shows transverse and cross sections, with block diagram inserts, of an NMR apparatus and method where the present invention may be used to advantage. An industrial process line IPL has material flowing as indicated by arrow A. Some of the material is captured by a probe P and fed through an inlet line LI to a sample region S1. The region is defined by a tube 98 typically about 30 cm long made of an essentially non-magnetic, nonconducting material which does not itself generate substantially interfering free induction decay (FID) signals. The tube material can be, for example, glass, certain ceramics, certain plastics, or hybrids thereof. The sample region is defined between inlet and outlet valves V1 and V2. Gas jets J are also provided. These jets are pulsed on/off repeatedly to agitate fluent sample materials during sample admission and expulsion. A region S2 is the critical portion of the sample. It is surrounded by a sample coil 100 tuned to resonance and driven by a tuning circuit 102 and related transmitter/receiver controller 104. Grounded loops 101 are Lenz Law shields which are provided above and below coil 100 to help shape the field of coil 100, i.e., to contain the field established by an excitation pulse. The controller 104 includes an on-board microprocessor and required power supply elements, memory, program and I/O (input/output) decoding suitable to interconnect to the hardware shown and to an external microcomputer 106 with associated memory, a keyboard 108, a monitor (or other display) 110, a recorder 112, and/or a process controller 114 (to control the process at IPL). The operator initiates and controls operation from the keyboard 108 and the resulting data and signals are subsequently shown on the display 110 and utilized in the recorder 112 and/or the controller 114. The computer 106 also controls instrument operation conditions.

The region S2 of tube 98 and coil 100 are in a static, but adjustable, crossing magnetic field defined by a magnetic assembly 116 which comprises a yoke 118, pole pieces 120, surrounding Helmholtz coils 124, and a coil current generator 117. The critical sample region S2 of the tube 98 and magnet are contained in a metallic (but non-ferromagnetic) box 126 with highly thermally conductive face-plates 128 and internal partitions 130 and overall mass related to each other to minimize harmonics and other interferences with a signal emitted from coil 100 to a sample and/or returned from the sample for pick-up by coil 100 and its tuned circuit 102 and transmit/receive controller 104.

Figure 1B:
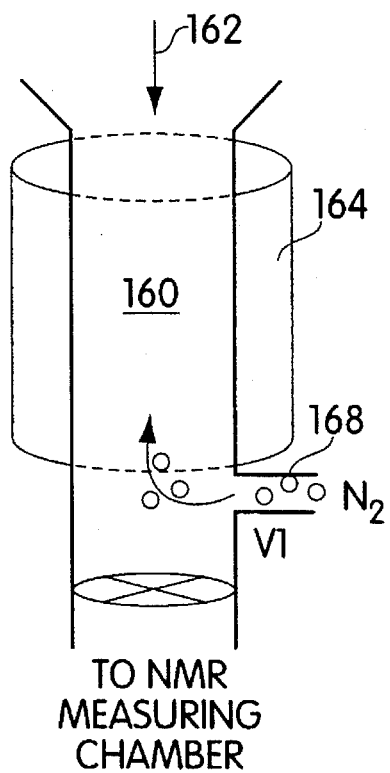
Figure 1C:
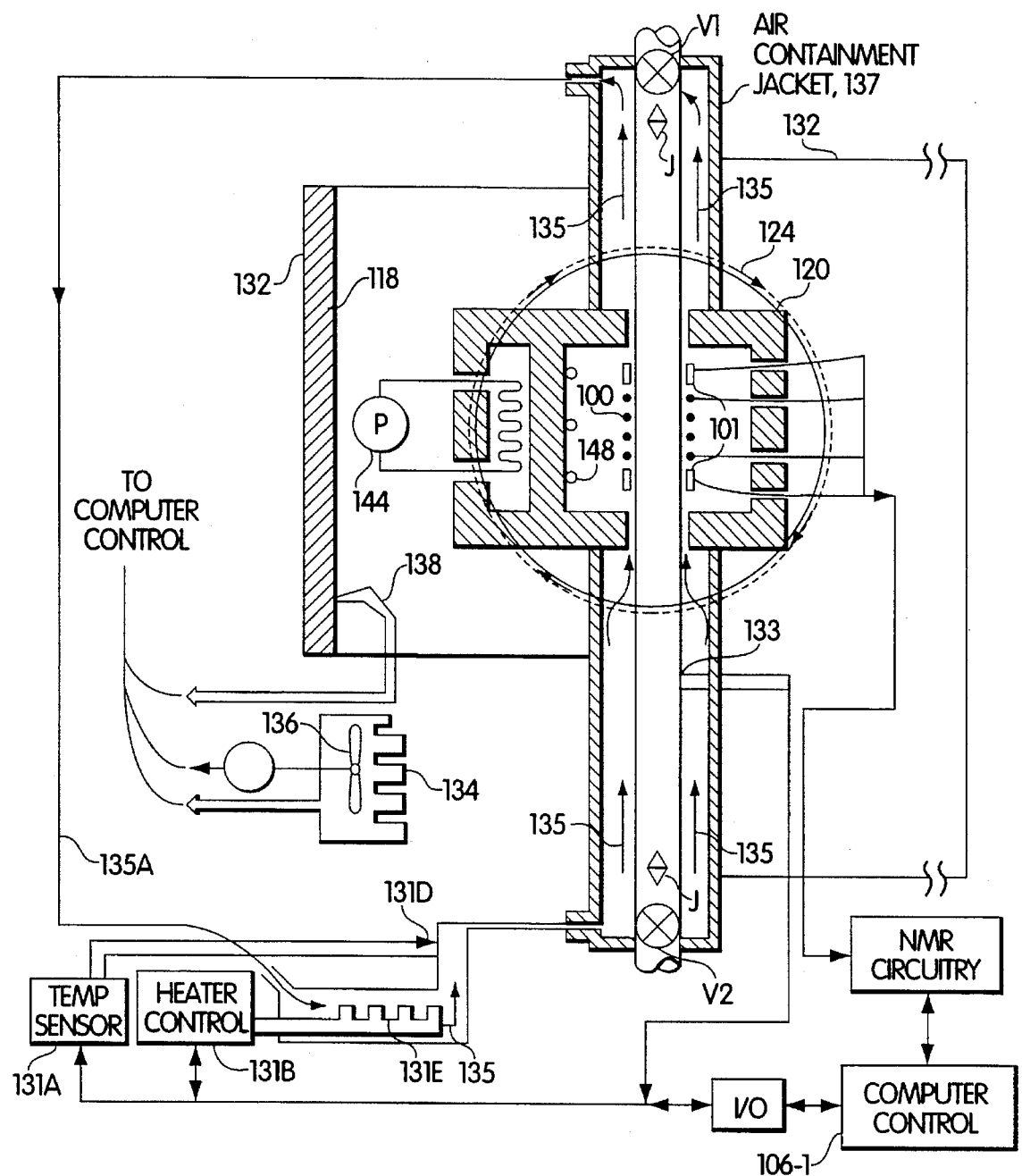

The magnetic assembly, including yoke 118, and other parts therein as shown on FIGS. 1A and 1C, is in turn contained in an environmental control chamber 132 with optional inert gas fill and purge controls (not shown), an internal electrical heater 134, a motor M driving fan 136, and a temperature sensor 138 in the air stream whose temperature is reflective of the temperature at pole pieces 120 and in the region surrounding the air curtain containment jacket 137. Additionally, there is a heated chamber shown in FIG. 1B where the sample is heated prior to introduction into the NMR sample chamber. A thermal controller 140 processes temperature signals from the sensor 138 to adjust heating/circulation at the heater/fan 134/136 as a coarse control and to adjust current through the Helmholtz coils 124 at magnet pole pieces 120 as a sensitive and fast fine control, as well as implementing general control instructions of computer 106. Further thermal stabilization is provided by a temperature controlled air curtain consisting of temperature controlled air 135 circulating inside an air containment jacket 137, completely surrounding the sample region under NMR measurement. The temperature of the air curtain is controlled by the heater thermal control 131B and temperature sensor 131A via 131D according to control parameters received from CPU 105-2 (I/O). Sample temperature is measured by temperature sensor 133 from which an external computer system 106 determines the desired air curtain temperature set point to be conveyed to heater thermal control 131B.

While the terms "air" and/or "air curtain" are used herein, it should be understood that other gas or liquid environments can be utilized.

FIG. 1B is a schematic outline of the heating chamber 160. The sample is fed (as indicated at arrow 162) into the chamber. There is a heating element 164 surrounding the chamber with its temperature set about 10 or so degrees centigrade higher than a mobility enhancing temperature known for the specific material. The temperature may be looked up in the below-mentioned text. The mobility enhancing temperature of a polymer material (e.g., a plastic such as polypropylene, polyethylene, and polystyrene) is defined herein as follows. It is the temperature that enhances precision and reliability for property measurements such as measurements of viscosity, molecular weight, melt index (MI), flow rate ratio (FRR), and melt flow (MF). Molecular weight, MI, FRR, and MF are closely related. Polymers generally have higher mobilities and an enhanced NMR response when at the mobility enhancing temperature. The mobility enhancing temperature is a minimum or threshold temperature in that there is a temperature range extending above the mobility enhancing temperature where the benefits occur without the sample handling problems associated with molten polymers. The mobility enhancing temperature is further defined and explained in the next paragraph.

The mobility enhancing temperature is the temperature at or above the "glass transition" temperature ($T_g$) for amorphous polymers (e.g., polystyrene), and at or above the "crystalline transition" temperature ($T_\alpha$) but below the "melting temperature" ($T_m$) for both crystalline and semi-crystalline polymers. $T_g$, $T_\alpha$, and $T_m$ are defined herein as temperatures where the following physical phase transitions take place. At the glass transition temperature ($T_g$), the fractional free volume for amorphous polymers increases appreciably and the polymer chains start undergoing rapid, almost isotropic motion. Amorphous polymer at this temperature has not melted and still retains a solid-like appearance to the lay observer. This state is sometimes referred to, in the art, as "rubbery". As a result, the NMR parameters, including time constants (T2's), are influenced. This enables better correlation with, for example, viscosity and MI or MF. For both crystalline and semi-crystalline polymers, it is necessary to carry out NMR measurements at or above the crystalline transition temperature ($T_\alpha$) in order to influence the NMR parameters and obtain better estimations of, for example, viscosity and MI or MF. In the case of a semi-crystalline polymer, the melting and crystalline transition temperatures are greater than the amorphous glass transition temperature. Adjusting the sample temperature to such temperatures as just described enhances NMR precision and reliability for at least the measurements of the above-identified properties and generally for other physical property measurements performed via NMR techniques. The specific temperatures as they relate to specific polymers are found in various handbooks and textbooks such as *Textbook of Polymer Science* by Fred W. Billmeyer, Jr. (Wiley-Interscience, a Division of John Wiley and Sons, Inc., 2nd ed., 1971). Again, these temperatures generally are collectively referred to herein as the mobility enhancing temperature.

The polymers of particular interest herein are polypropylene, polyethylene, and polystyrene. In general, two types of polystyrene exist: "crystal" and "extended". Extended polystyrene is also referred to as "impact" or "rubber extended". The property of polystyrene, regardless whether it is crystal or extended, of most importance herein is MI. Crystal polystyrene typically has oil added to it, and thus the percentage of oil (oil %), in addition to MI, can be a property of interest to be measured when the sample is a crystal polystyrene. Extended polystyrene typically also has oil and/or rubber added, and therefore MI, oil %, and the percentage of rubber (rubber %) are measurements of interest for extended polystyrene samples. Other polymers that can be tested accurately with the NMR system according to the invention include Ethylene Propylene Rubber, Acryonitrile Butadiene Styrene (ABS) plastic, and Ethylene Vinyl Acetate (EVA) copolymer.

Still referring to FIG. 1B, the sample fed (as indicated at arrow 162) into the chamber remains there long enough to ensure that the sample has achieved the proper temperature. The temperature need only be within a few degrees of an actual set point. To further ensure proper and uniform heating, a heated temperature controlled nitrogen stream of gas 166 or air is introduced via a port 168 in order to fluidize the material. After two (or more) minutes the sample is introduced into the NMR measuring chamber S2 by opening the valve V1. The gas in introduced in a direction and with a pressure to create a turbulence in the material that induces movement of particles and homogenization of material temperature.

Figure 2A:
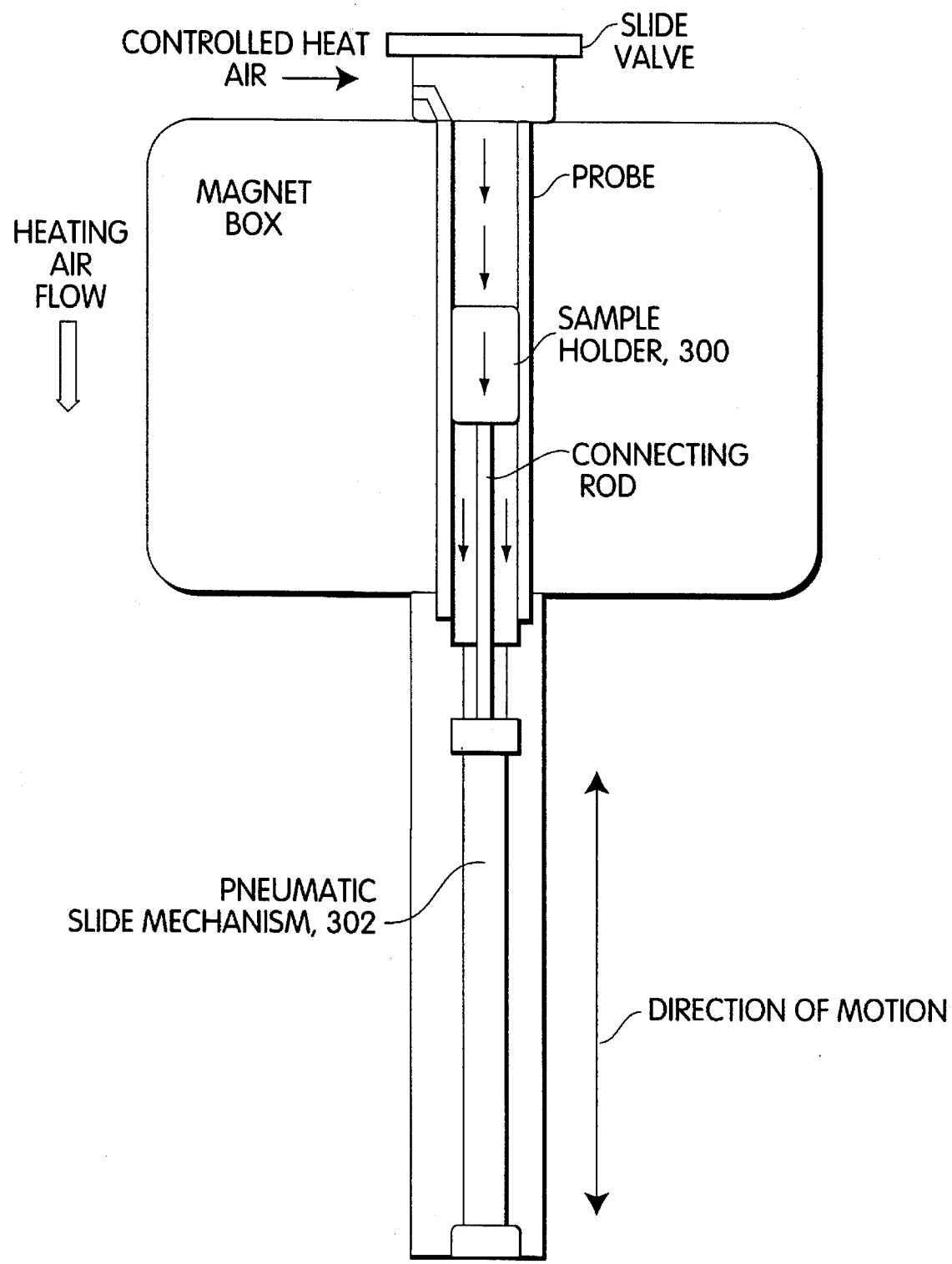
FIGS. 2A–2D are diagrams of other embodiments for handling samples.
Figure 2B:
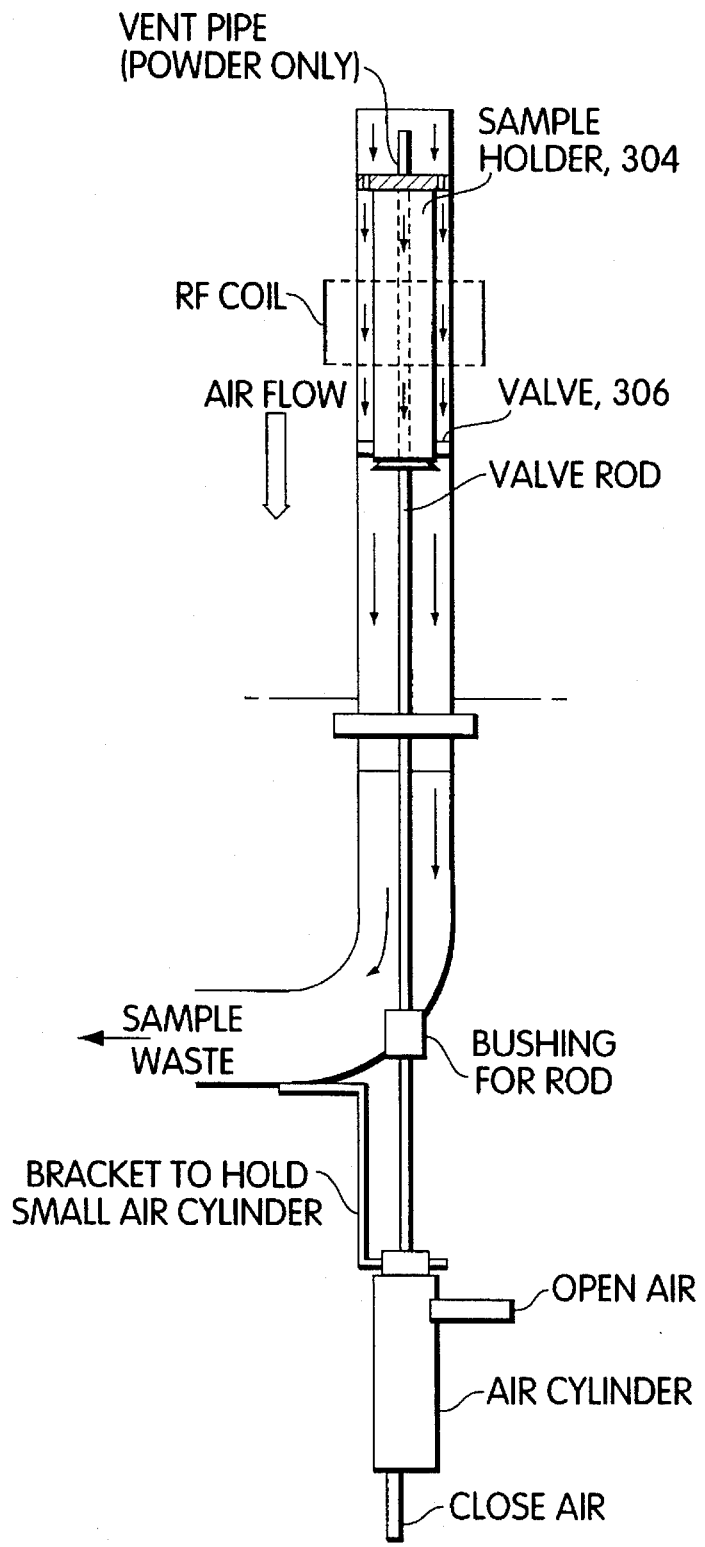
Figure 2C:
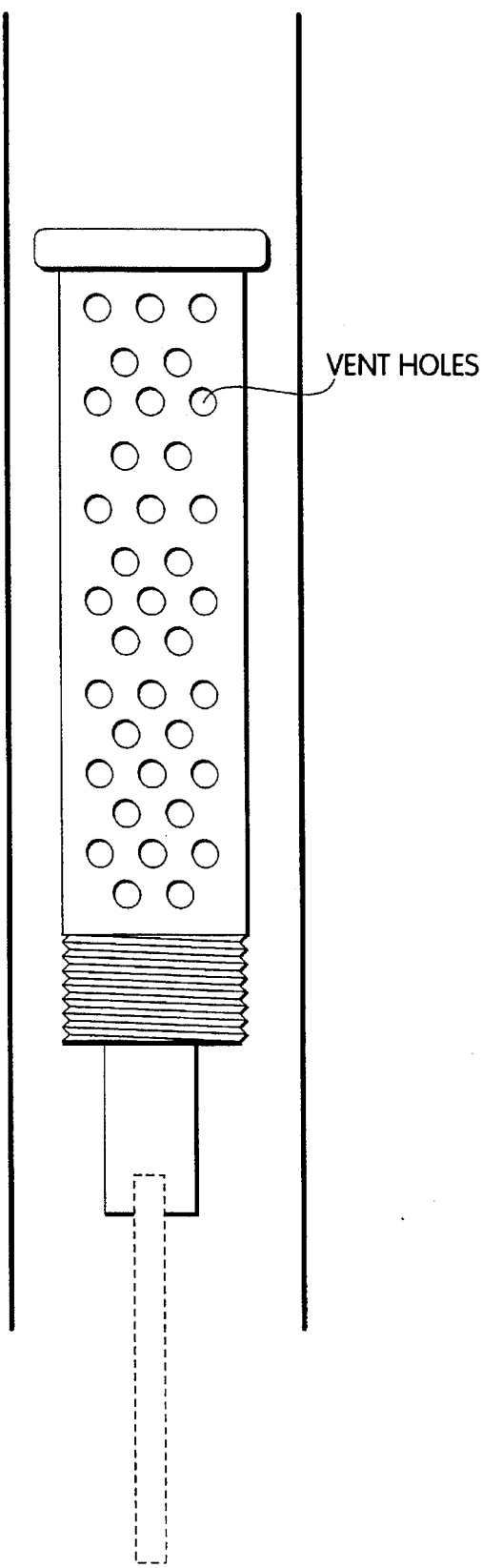
Figure 2D:
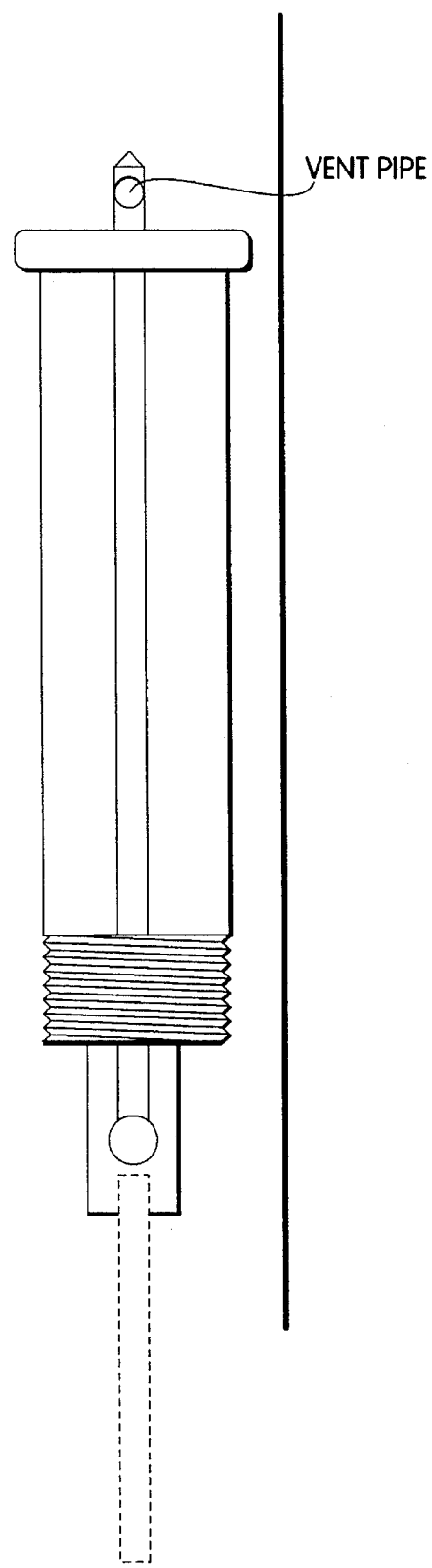

Other embodiments for handling (e.g., heating, measuring, and discarding) the samples are possible. For example, referring to FIGS. 2A–2D, the sample is heated inside the probe region prior to the measurement. In general, these other embodiments are better suited to a non-real time, off-line, laboratory environment. In the embodiment illustrated in FIG. 2A, the sample is contained in a sample holder or "basket" 300. The holder 300 itself may be positioned on an air-cylinder driven mechanical sliding mechanism 302 for physically removing the sample after each measurement by lowering the basket 300 and removing the sample mechanically and by air jets. This arrangement is particularly suitable for those samples that stick together during the heating time and cannot be removed by simple air pressure and gravity. In another embodiment illustrated in FIG. 2B, a sample holder 304 is permanently fixed in position in the center of the probe and a valve 306 is located at the bottom of the sample holder 304. The sample is removed by lowering the valve, and the sample is forced out by the heating air driven from the top. The controlled heating air enters the actual probe chamber from the top, and it is forced around and through the sample for the case of pelletized material (FIG. 2C) or around and through a central vent pipe for the case of powdered material (FIG. 2D). The actual heating time is predetermined in each case for adequate heating to the desired temperature. Sample temperature is determined by a thermocouple located just above the sample.

Figure 3:
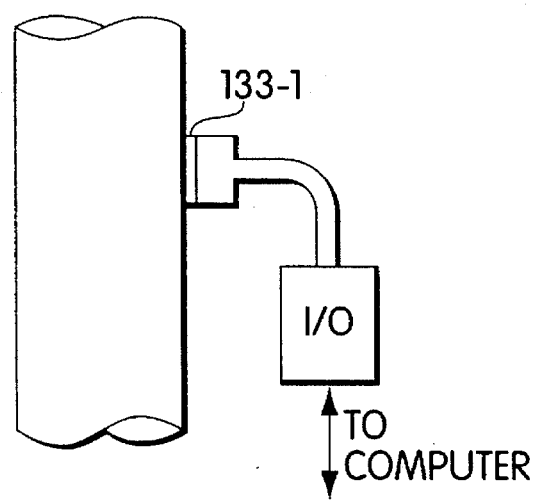
FIG. 3 is a diagram showing a sensor for measuring the sample temperature.

In FIG. 1C, all the electronics and computers and other elements of the system controller are grouped for simplicity of description into one block 106-1. The temperature of the sample chamber is measured by a temperature sensor 133, such as a silicon junction device or thermocouple, embedded in the chamber wall. FIG. 3 shows another preferred embodiment where the sensor is an infrared (heat) sensor with a window through the sample chamber wall whereby heat radiation impinges the sensor. The sensor signal is fed through an I/O interface to the computer portion of the controller 106-1. In another preferred embodiment, the I/O interface may contain an analog-to-digital (A-to-D or A/D) converter separated from the computer and/or input to the computer via some other communication port, e.g., a serial port. The computer can interrogate the sensor and measure the temperature at any time, typically at the start of the NMR measurement time period and again at the end. In response to a temperature change during the NMR measurement, the system adjusts the temperature through the heater 131E. The temperature of the heated air 135 is measured by the sensor 131A via 131D which is placed in the air path 135. The controller 106-1 maintains the sample temperature constant through the heated air within the air curtain. These two means give the entire system the ability and capacity to maintain the sample temperature essentially constant while the environment air around the NMR system changes.

As discussed before, to enable better correlation of the NMR data with viscosity and MI or MF (average molecular weight), amorphous polymers are measured at or above the glass transition temperature, and crystalline and semi-crystalline polymers are measured at or above the crystalline transition temperature but below the melting temperature (i.e., polymer samples are measured at the mobility enhancing temperature as defined above).

Referring back to FIG. 1A, the strength, consistency, and constancy of the magnetic field between poles 120 in the region S2 of the sample is thus controlled by a uniform base magnetic field modified by a small correction generated by Helmholtz coils 124 in the entire region S2. The Helmholtz coils 124 are energized by the coil current controller 177 to accurately trim the final magnitude of the field in which the sample is placed. This field is the vector addition of the fields due to the magnet poles 120 and the Helmholtz coils 124.

The controller 117 sets the current through the Helmholtz coils 124 using current generators. The coils 124 are wound around the magnet pole pieces such that the magnetic field created by the current in the coils 124 can add to or subtract from the field created by the magnet pole pieces. The magnitude of the current through the coils 124 determines the strength of the field added to or subtracted from the field due to the magnet pole pieces (and related yoke structure) alone.

The actual determination of the current through the Helmholtz coils is accomplished by carrying out the magnetic energy and resonance techniques hereinafter described in preliminary runs and adjusting Helmholtz current until the maximum sensitive resonance is achieved. Operating the system this way at resonance or on resonance is the preferred mode of system operation. In another embodiment, the Helmholtz current is set off resonance by a given offset of about 0.1–3 KHz.

The major elements of electrical controls are tuner 102, including coils 100 and 101 and variable capacitors 102-1 and 102-2, resistor 102-3 and diodes 102-4 and constructed for tuning to Q of twenty to sixty to achieve coil 100 resonance, and control 104 including a transmit/receive switch 104-1, a transmitter 104-2 and receiver 104-3, a crystal oscillator 104-4, gated pulse generator (PPG) 104-5, and phase shifter 104-6. The crystal provides a nominal twenty Megahertz carrier which is phase modulated or demodulated by the MOD, DEMOD elements of transmitter 104-2 and receiver 104-3. The receiver includes variable gain amplifier elements 104-31 and 104-32 for operation. The analog signals received are fed to a high speed at least 12 bit flash A/D converter 105-1 and internal (to the instrument) CPU element 105-2, which provides data to an external computer 106 which has a keyboard 108, monitor 110, modem 109, recording elements 112, and process controller elements 114, e.g., for control of valves VI, V2 via valve controls 115 and/or to coil current controls 117, all via digital-to-analog (D-to-A or D/A) converters (not shown).

The analog signal FID curve is conditioned by a Bessel filter which acts as a pre-filter and an anti-aliasing filter as the subsequent sampling (i.e., digitizing) is usually done at 10 MHz. After digitization, the signal may be time smoothed by a Fast Fourier Transform, Savitsky-Golay, or other filter or filtering procedure. The combination of these filters produces a relative improvement in signal-to-noise ratio which generally enhances the accuracy of the NMR system.

The excitation of coil 100 and excitation-precession of the sample's proton content and subsequent relaxation/decay produces a received FM signal that, after demodulation, controlled gain amplification, and A/D conversion produces the free induction decay (FID) curve.

As indicated earlier, preferred embodiments are found in the NMR instrument whether operated in resonance or out of resonance, including those preferred embodiments found in the above-listed related patents and patent applications which have been incorporated by reference hereinto. The following preferred embodiment describes a system and method for the analysis of polymers, in particular, polypropylene, polyethylene, and polystyrene.

Figure 4:
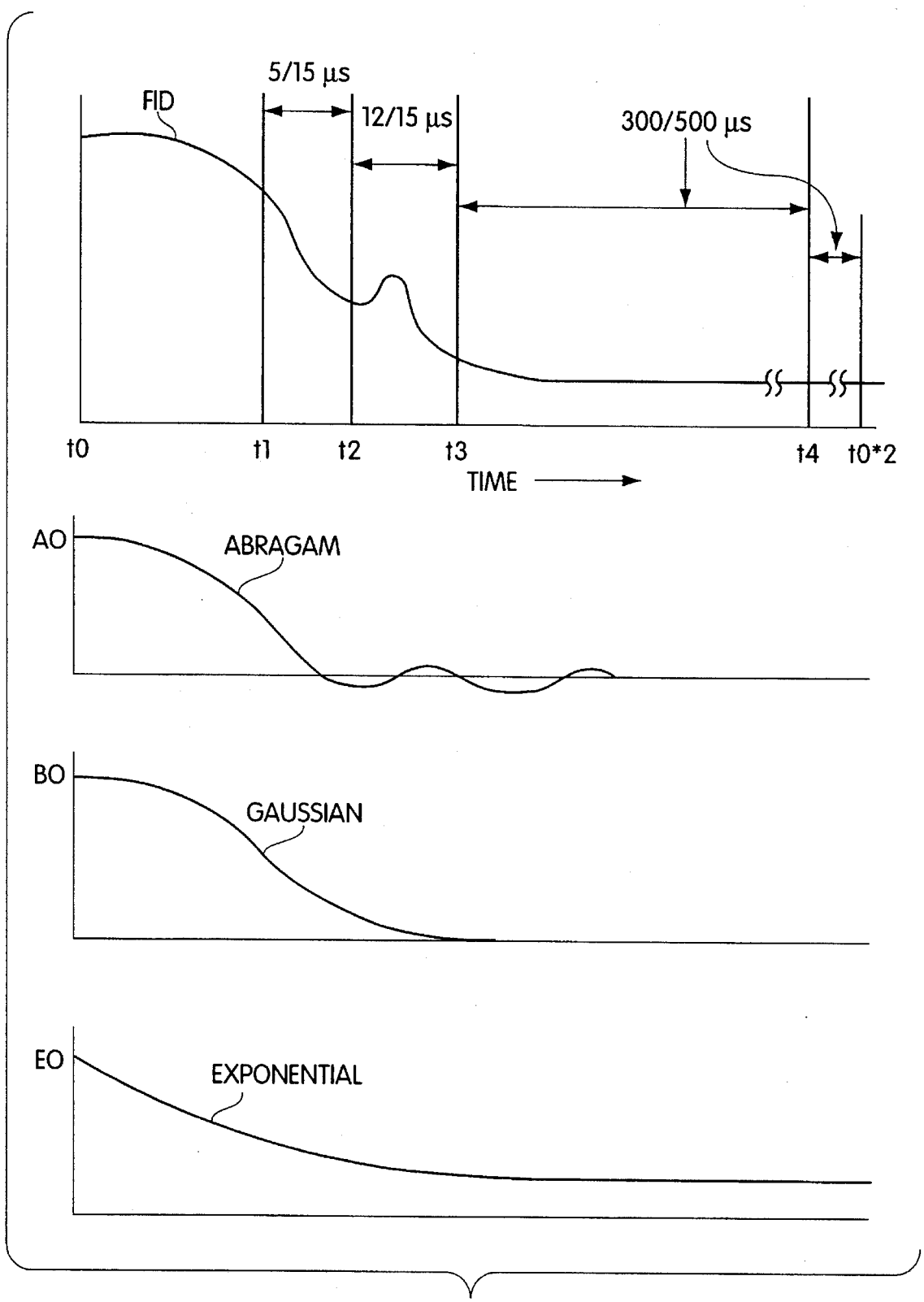
FIG. 4 is a graphical representation of a free induction decay (FID) curve and its component curves measured for polyethylene.

Referring to FIG. 4, the digitized FID curve data for the material under test (e.g., polyethylene, polypropylene, or polystyrene) are transmitted to the external computer 106 where a computer program finds the best coefficients of the component curves to fit each component of the digitized FID curve. In the disclosed embodiment, there are three components: an Abragam, a Gaussian, and an exponential. Other embodiments have more or less than three component curves and other curve types such as modified exponential and/or trigonometric. The determination of the types of curves which make up the FID curve is important because, once the curves are known, they can be extended back to a time origin (shown as A0, B0, and E0 at t0) which is close to the center of the transmitted burst signal. This is important since there are saturation effects of the instrument's electronic gear which occur during and immediately after the excitation burst signal. During this time, measurements cannot be accurately taken, yet the region of interest under the curve, which is a measure of the number of nuclei in the sample, extends from the immediate end of the excitation burst to where the curve is too small to be digitized or is in the noise.

Again, the entire FID curve is decomposed into component curves. Coefficients defining the equations of the component curves are derived by using an iterative process based upon the Marquardt-Levenberg (M-L) approximation technique. The derivation is applied automatically through a structured realization in software. This M-L technique is used to determine the magnitude of all the parameters, constants, frequencies, etc. which best fit the FID curve. M-L is an iterative technique where the entire curve is determined at once. The M-L iteration process performs the curve fitting by attempting to minimize the Chi-Squared error function (the sum of the squared differences between the measured data points and the data points from the derived equation). The results of the M-L approximation are accepted if the Chi-Squared error is small enough and if the number of iterations to reach an acceptable Chi-Squared error does not exceed a preset limit, usually about 30. If the error is not small enough, the M-L fitting procedure may be re-applied with a different set of starting assumptions. If this re-attempt also fails, the sample is discarded and a new sample obtained. The M-L technique is documented in the following references: *Ind. Appl. Math.*, vol. 11, pp. 431–444 by D. W. Marquardt, 1963; *Data Reduction and Error Analysis for the Physical Sciences* (New York, McGraw Hill) Chapter 11 by Philip R. Bevington, 1969; and *The State of the Art in Numerical Analysis* (London: Academic Press, David A. H. Jacobs, 1977), chapter III.2 by J. E. Dennis. As applied to the measurement regime of interest herein, in a preferred embodiment of the present invention, the selected parameters taken from the derived curves are the y-axis intercept ratios, time constants, frequency terms, and other parameters described below.

Other known-in-the-art iterative techniques which may be applied instead of, or with, the Marquardt-Levenberg include: Gauss-Jordan and "steepest descent" (found in the above J. E. Dennis reference); Newton-Raphson (known in the art); "partial least squares"; or similar techniques including combinations of these techniques.

One of the major difficulties in making use of iterative curve fitting techniques (such as Marquardt-Levenberg) is their tendency to reach incorrect solutions. Such solutions frequently (but not always) contain parameters which would imply a negative quantity of protons or an exponential "decay" which grows with time. These incorrect solutions lead to serious errors in the result found for a physical sample, for example, the density or flow properties (e.g., MI) in polyethylene or the extent of tacticity or MF in polypropylene.

Once the equation of the FID curve is known, each component curve can be extrapolated back to the midpoint of the excitation signal to establish the intercept of each said component curve.

The resulting data utilized in the computer 106 (FIGS. 1A and 1C) is the equation for the FID curve as composed of a number of component curves. Each of these curves (and their intercepts) has been experimentally and theoretically related to particular nuclei of interest. In particular, when the FID curve equation is determined, the ratios of the y-axis intercepts, the cross product and squares of these ratios and the decay times for each of the curve components, and the product temperature form one or more multidimensional models for the property.

Calibration of the system is accomplished by first measuring a number of known samples and using the M-L technique to derive the model equation constants associated with each known sample. Various non-linear transforms may then be applied to these constants, usually with the goal of linearizing their relationship to the dependent (i.e., predicted) parameter. Useful non-linear functions include exponential, logarithmic, powers, and cross products of the independent (i.e., measured) parameters.

Figure 5A:
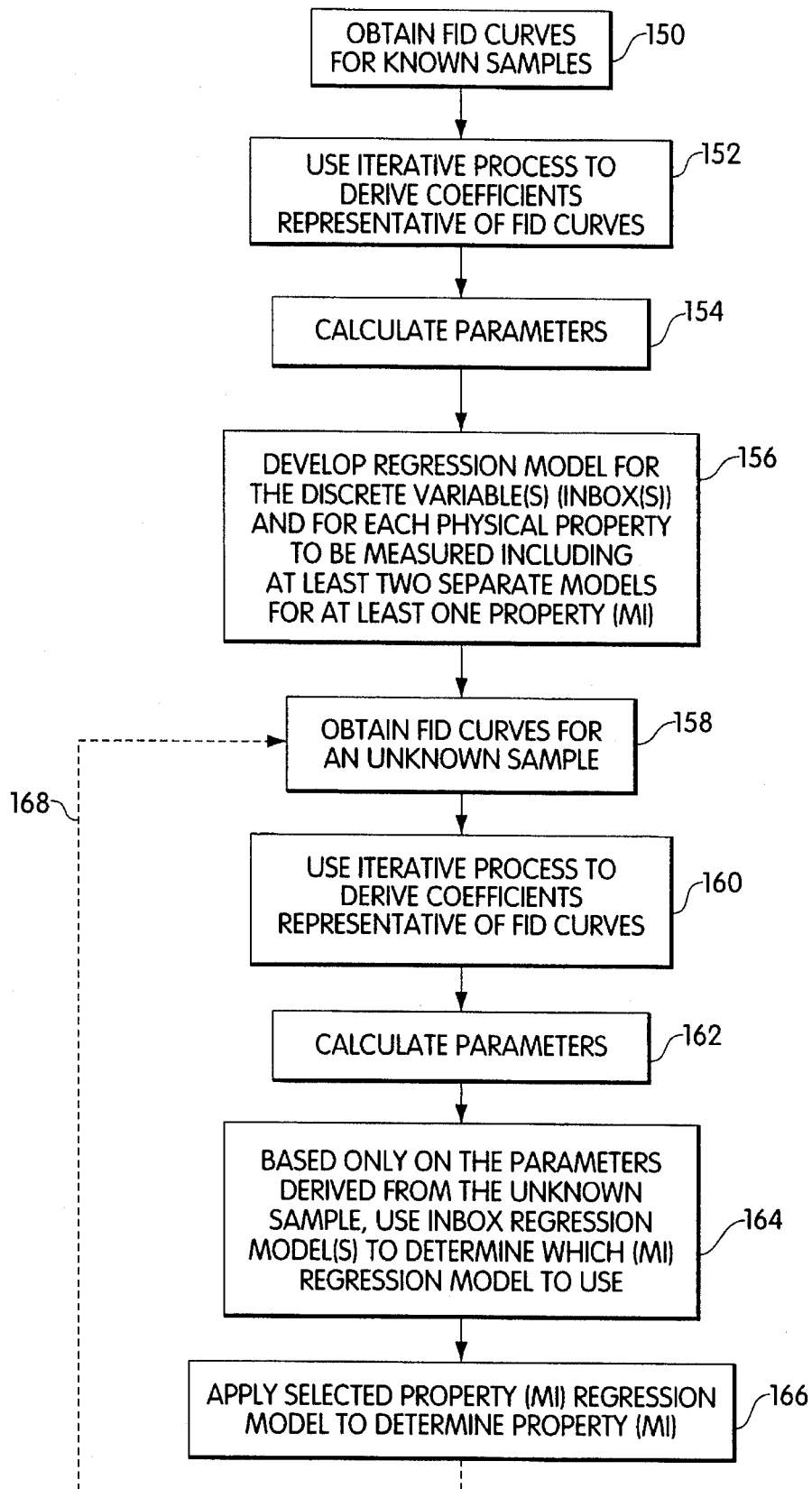
FIG. 5A is a flowchart of steps performed according to the invention to determine properties of a polymer sample.

FIG. 5A is a high-level flowchart of steps performed according to the invention to determine properties of a polymer sample (e.g., a sample of plastic such as polypropylene, polyethylene, or polystyrene). The NMR system of the invention develops one or more regression equations or models for a given property (e.g., two models for MI, one model for density, etc.) during a calibration procedure using known samples (steps 150–156). The invention relates to those polymer properties for which two or more regression models are developed during calibration with known samples. In a preferred embodiment, at least two property (e.g., MI) regression models (e.g., $MI_1$ and $MI_2$) are developed (step 156). A regression model for each of one or more discrete (i.e., two-valued) variables also are developed during calibration (step 156), and these models allow a prediction to be made about which of the plurality of MI regression models should be used for any particular unknown sample (step 164). If there are two regression models for the particular polymer property of interest, only a single discrete variable regression model is needed, and the two possible values of the variable correspond to the two property models. That is, in the case of two property models, the single discrete variable model yields a value (one of the two possible values) which corresponds to the property model that will produce the most accurate measurement of that property for an unknown sample. However, if there are N regression models for the property of interest and N is greater than two, N discrete variable regression models are used and each one corresponds to a different one of the N property models. In this N>2 case, the property model that corresponds to the discrete variable regression model yielding the largest value is selected as the property model that will produce the most accurate measurement of the property of interest for the unknown sample. In either case, after having selected one of the plurality of property regression models by using the discrete variable regression model(s) (step 164), the selected property model is applied to data derived from the unknown sample to determine or estimate a value of the property of interest (e.g., MI) of the unknown sample (step 166). In accordance with the invention, this property measurement is acceptably accurate. In one embodiment, an acceptable MI measurement made by the NMR system has a standard deviation less than 10% and typically about 5–7% or less.

This standard deviation is the standard deviation between the MI estimation obtained by the NMR system according to the invention and the "actual" MI value (e.g., the MI value obtained by a manual laboratory ASTM method). The "actual" MI value can be determined "off-line" in the laboratory with a laboratory instrument.

The discrete variable mentioned in the paragraph preceding the above paragraph is created ahead of time and prior to model making based on, for example, laboratory density and MI data for polyethylene or laboratory solubles/tacticity and MF for polypropylene. This data can be gathered from various sources such as users of NMR systems conforming to the descriptions in the above-listed related patents and patent applications. For example, the discrete variable can have a certain value (e.g., 1) for polyethylene with a density$\leq$0.9225 grams/milliliter and an MI$\leq$1.25 and another value (e.g., 0) for any other polyethylene grade. It should be understood that more complex conditions might be applied such as density and/or MI within a certain range (e.g., 0.91<density<0.9225 and 0.2<MI<1.25). This discrete variable (or variables) is referred to sometimes herein as INBOX because its value indicates whether or not the material is inside of the "box" defined by the above-identified density/MI range. Using such a discrete variable or variables (i.e., $INBOX_1$, $INBOX_2$, . . . ) results in improved polymer property measurements (e.g., MI measurements with a standard deviation less than 10% and typically about 5–7% or less) regardless whether an unknown sample is outside or inside of a particular range or region (e.g., the density/MI range identified above). That is, material for which the NMR system might previously have produced unacceptable property (e.g., MI) estimations (e.g., plastics falling within the above-identified range) can now be tested with the NMR system according to the invention and an acceptable, useful MI estimation is achieved.

It is important to note that the one or more "boxes" corresponding to the one or more INBOX variables need not be square or rectangular. In general, each "box" can have any shape, and each identifies a particular subset of the data. Each "box" is in general a range or region.

Figure 5B:
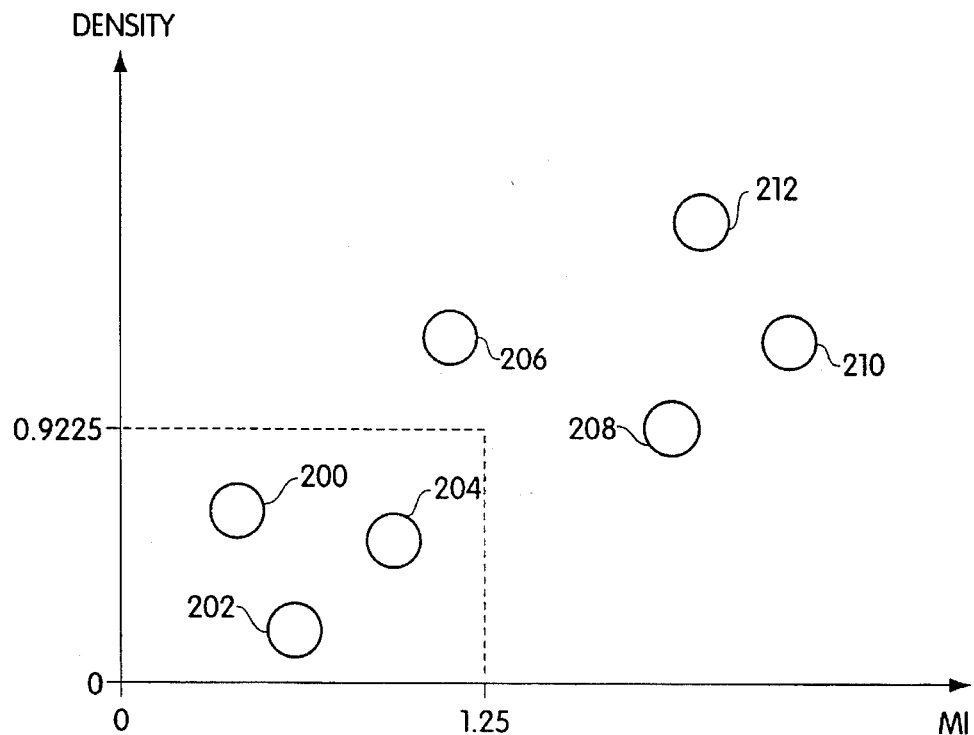
FIGS. 5B and 5C are graphs of NMR measurements of density versus NMR measurements of melt index (MI) showing various plastic grades (polyethylene in this case).

Referring to FIG. 5B, it was discovered that some plastic materials (e.g., polyethylene without hydrogen added during polymerization as indicated by circles 200, 202, and 204) fall within a box defined by the above-given density/MI range, whereas other plastic materials (e.g., polyethylene with hydrogen added as indicated by circles 206, 208, 210, and 212) fall outside of the box. For the products outside of the box, the NMR system produced acceptable MI estimations (e.g., a standard deviation of 8.5%) by prior data analysis schemes. For the products inside of the box, however, the NMR system produced unacceptable MI estimations (e.g., a standard deviation of about 10–12% or higher). The invention addresses this problem by modifying the NMR system such that it now can more accurately estimate MI, and a variety of other polymer properties, regardless whether the material being tested is within or outside of the box. The NMR system according to the invention automatically produces polymer property (e.g., MI) estimations which are acceptably accurate (e.g., MI measurements less than 10% and typically 5–7% or less) for materials falling both within and outside of the box.

In general, the "grouping" or association of certain polymers to a particular model is made based on or determined by significant chemical properties or process conditions for that polymer group.

In one embodiment, if the sample is a polyethylene sample falling within the range, a certain MI regression model is used. If the sample falls outside of the range, a different MI regression model is used. Regardless of the particular plastic being sampled, the invention automatically selects the MI model which results in the most accurate MI measurement.

Figure 5C:
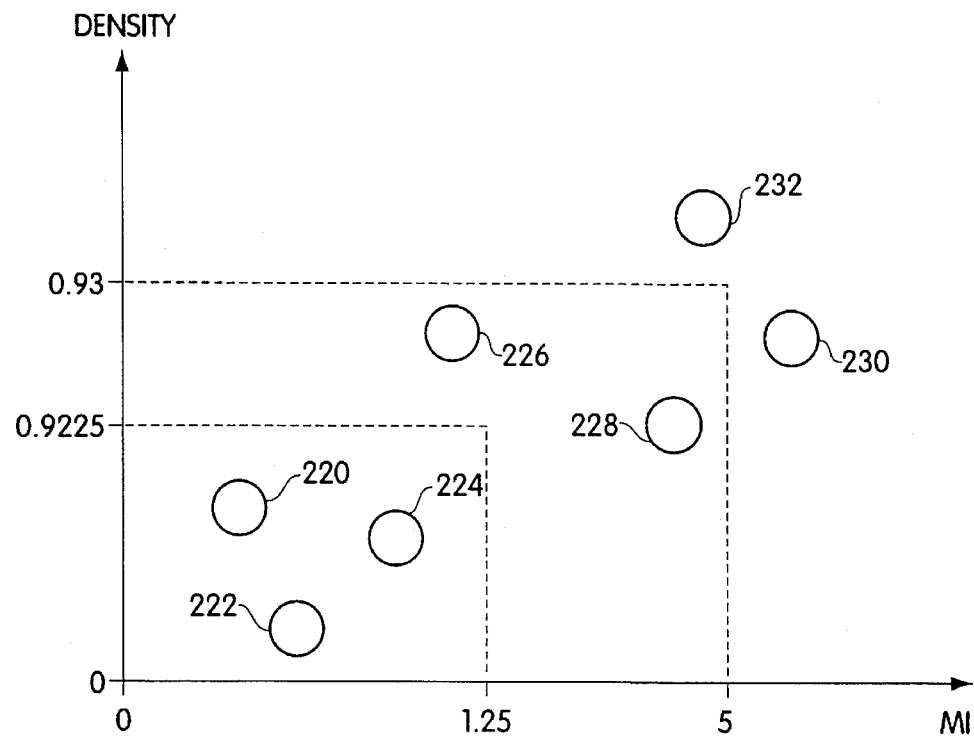

Referring to FIG. 5C, it was discovered that some plastic materials (e.g., material indicated by circles 220, 222, and 224) fall within a first box defined by the above-given density/MI range, whereas other plastic materials (e.g., material indicated by circles 226 and 228) fall outside of the first box but inside of a second box, and still other plastic materials (e.g., material indicated by circles 230 and 232) fall outside of both the first and second boxes. A different INBOX variable is associated with each of the three regions. By using these three variables, it is possible now to estimate more accurately the particular polymer property of interest regardless of which box or region the material being tested falls into.

In one embodiment, if the sample is a polyethylene sample falling within the middle range, the MI regression model associated with that range will automatically be selected by the corresponding variable model yielding the largest value of the other two variable models, and that MI model is then used to achieve the most accurate MI measurement possible. Note that if the other INBOX variables yield values that are too large, no MI model will be selected and thus no MI estimation or prediction will be made in these cases.

In accordance with the invention, a plurality of regression models for a property other than MI (e.g., xylene solubles, density, rubber/oil content, FRR, or MF) can be developed during the calibration procedure (steps 150–156 of FIG. 5A). For example, two or more regression models for rubber content (e.g., $R_1$ and $R_2$) can be developed. In this case, the discrete (e.g., two-valued or Boolean) variable regression model allows a prediction to be made about which of the two rubber content regression models should be used for any particular unknown sample. After the rubber content model is selected by using the discrete variable model, the selected rubber content regression model is applied to data derived from the unknown sample to determine the rubber content of the unknown sample.

Referring again to FIG. 5A, the steps performed in a preferred embodiment of the invention generally are as follows. Samples with known types, properties, and quantities of target nuclei (including flow rates such as MI, FRR, and MF in plastics such as polypropylene, polyethylene, and polystyrene) are introduced into the NMR system (step 150). The FID curve is digitized via a flash converter of at least 12 bits accuracy and the result is stored in memory. The M-L iterative process is then used to derive the curve coefficients from the stored FIDs to a given Chi-squared error and iteration limit (step 152). The various non-linear transformations to be used are then determined to arrive at the various parameters (step 154). The types, properties, and quantities of target nuclei in the known samples are then related to the parameters by a regression against these transformed parameters to arrive at a regression equation or model for the discrete INBOX variable or variables and for each physical property of interest including at least two separate models for at least one polymer property such as MI (step 156). These models are stored in the NMR system of the invention in memory.

Unknown samples can now be introduced into the NMR system. The FID curve for an unknown sample is recorded and digitized (step 158). The curve coefficients are then derived (step 160), and the parameters are calculated (step 162). Based only on the parameters of the unknown sample (and not on any external user-entered information), the INBOX regression model(s) is/are used to arrive at a particular value for the discrete INBOX variable(s) (step 164). This value (or values) corresponds to one of the polymer property (e.g., MI) regression models, and that model is selected (step 164). In the case of more than two regression models for a particular polymer property of interest, the same number of discrete INBOX variable regression models are used, and each INBOX variable model corresponds to a different one of the property models. In the case of just two property models, only a single INBOX variable model is used, and each value of the two-valued variable corresponds to a different one of the property models. In either case, the selected regression model for the property of interest is then applied to the parameters derived from the unknown sample to determine a value for that property of the unknown sample (step 166). The property can be estimated for other unknown samples by returning to step 158 and introducing into the NMR system the next unknown sample, as indicated by a dotted line 168.

Further details of the steps described generally above and with reference to FIG. 5A are presented below with reference to FIGS. 6A and 6B.

Figure 6A:
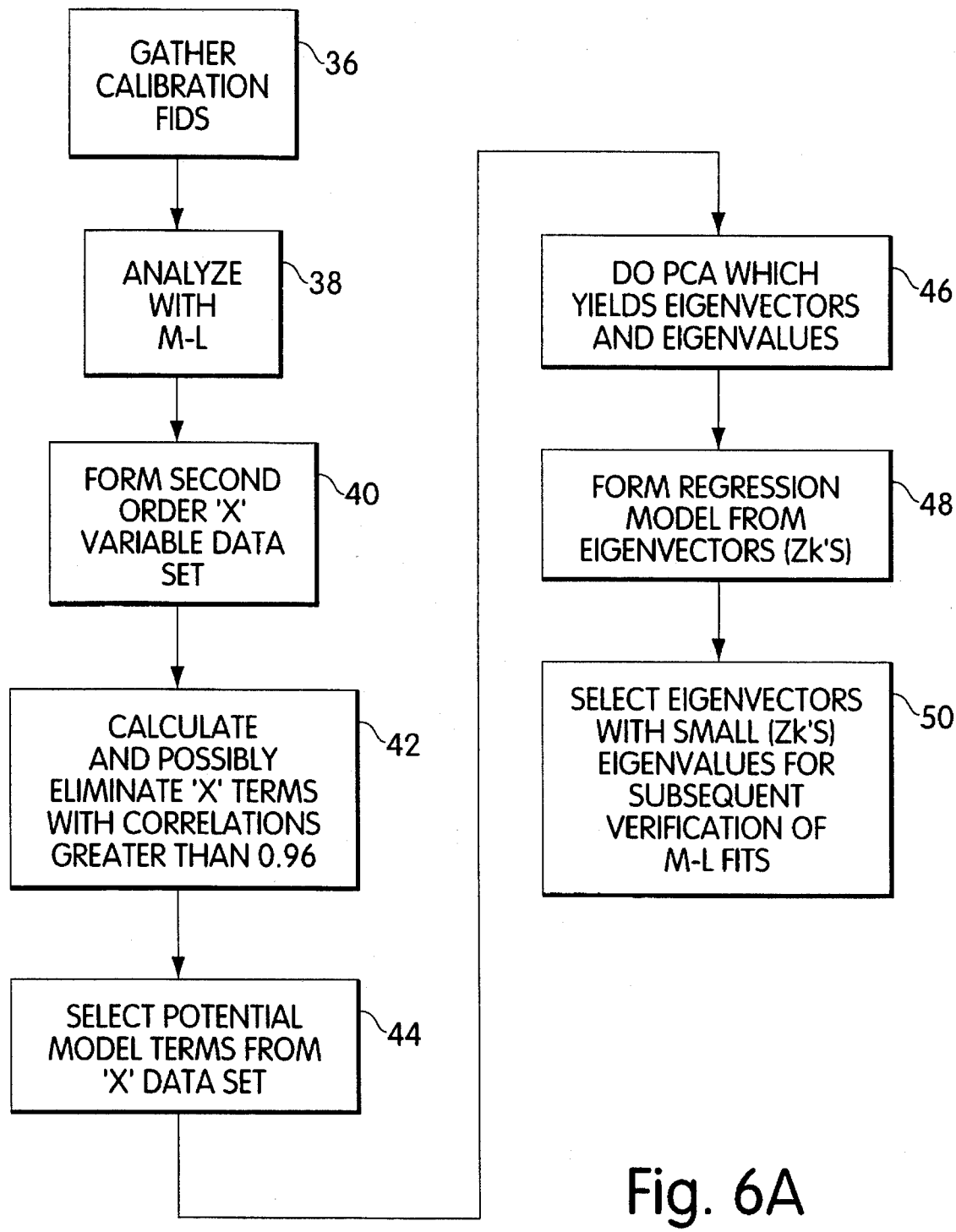
FIGS. 6A and 6B are flowcharts of steps, more detailed than those shown in FIG. 5A, performed in accordance with the invention to determine properties of an unknown polymer sample.

Referring to FIG. 6A, the first step 36 is to measure samples with known types, properties and, quantities of target nuclei, including flow rates (e.g., MI, FRR, and MF) in plastics (e.g., polyethylene, polypropylene, and polystyrene). This data gathering (step 36) may be done on-line or off-line. The FID curve is digitized via a flash converter of at least 12 bits accuracy and stored in memory. The step 38 is to apply the M-L iterative process to derive curve coefficients from the FIDs to a given Chi-squared error. In step 40, the second order "x" variables (i.e., the explanatory variables) are formed. These x variables can include various parameters such as ratios of Y-axis intercepts, squares and cross products of these ratios, decay times, and temperatures. Higher order combinations of these parameters also may be calculated. These x variables can be thought of as vectors in a multidimensional space where the space dimension is equal to the number of the explanatory variables. If there is no multicollinearity among the x variable data, the vectors are orthogonal in this space (i.e., all dot products are zero). As multicollinearity increases, the vectors move away from orthogonality. In the extreme case, there may be perfect correlation between two or more of the x variables and the vectors will lie on top of one another. An attempted regression analysis of such data would generate singular matrices. In step 42, x variable data with correlations above a certain threshold (e.g., 0.99) can be eliminated.

The next step (step 44) is to choose a set of potential explanatory variables, the x data, from the M-L derived time equations including second and higher orders of these variables. They are chosen by a stepwise technique or some other known technique. In a preferred embodiment, three different sets of x variables are selected and taken through the entire remaining steps (steps 46, 48, and 50) and the set giving the best results is used. In a preferred embodiment, the best result is that which results in the lowest adjusted standard deviation of error on the degrees of freedom. One of the three different sets is composed of all the x variables. The second set is formed by the known stepwise technique of adding each new variable and determining if that variable helped and then continue adding those variables that help. The technique is also applied in a backwise fashion where each previously added variable is retested in the presence of each new variable. The third set is formed by taking all independent variables and variables with correlations between selected low and high limits, usually 0.2 to 0.96.

The independent variables (the "y" variables) represent the property or characteristic of interest for the sample being tested. The y variables are related by a set of linear equations to the x or explanatory variables.

The next step (step 46) is to perform a Principal Component Analysis (PCA). Every linear regression model can be restated in terms of a set of orthogonal explanatory (x) variables, where the new variables are linear combinations of the original x variables. The new x variables are called principal components and are orthogonal, thus eliminating the problem of multicollinearity. The regression model equation using the original explanatory variables is $$Y = X\beta + u \qquad \text{(Eq. 1)}$$

where Y is an n-by-1 column matrix of n observations, X is an n-by-p matrix of n observations on p explanatory variables, $\beta$ is a p-by-1 column matrix of regression coefficients, and u is an n-by-1 column matrix of residuals. If it is assumed that the expectation of u is 0, and that the expectation of uu' (wherein u' is the conjugate of u) equals the variance times the identity matrix, and that X and Y have been centered and scaled so that the XX' and YY' are matrices of correlation coefficients, then there exists a matrix C, satisfying $$C'(XX')C = \Lambda \qquad \text{(Eq. 2)}$$

and $$C'C = CC' = I \qquad \text{(Eq. 3)}$$

where $\Lambda$ is a diagonal matrix with ordered Eigenvalues of XX' on the diagonal. The columns of C are the normalized Eigenvectors.

A new set of explanatory variables Z may be formed by Z=XC. These are summarized as $$Y = X\beta + u = XCC'\beta + u = Za + u \qquad \text{(Eq. 4)}$$

where the Z vectors are orthogonal.

This process (step 48) of transforming the x data into z data produces a diagonal matrix $\Lambda$ of Eigenvalues of the principal components. An Eigenvector of a square matrix A of order n is a nonzero vector v where $Av = \lambda v$, and the scalar $\lambda$ is called an Eigenvalue. Eigenvalues may be calculated for matrix A from $$|A - \lambda I| = 0 \qquad \text{(Eq. 5)}$$

where I is the identity matrix, and the corresponding Eigenvectors v may then be found by solving $(A - \lambda I)v = 0$. The Eigenvalues are sorted numerically from the largest (top left of the diagonal) to the smallest (bottom right). If strong multicollinearity exists, as it does for many of our explanatory variables, one or more of the lower right diagonal terms will be very small compared with the others and these terms may approach zero. If the Eigenvalue is sufficiently close to zero, the value of the corresponding z transform of the x data is also essentially zero, as given by $$Z_k = F_k(x1, x2, \ldots, xn) = 0 \qquad \text{(Eq. 6)}$$

where $F_k$ is the linear transform derived from PCA.

The relationships of Eq. 6 are used to test each M-L curve fit to determine whether the x values obtained from M-L comport with those in the calibration set (derived from the known samples). For this test, a standard set of parameters are used. The set includes five variables: $R_{ag}$ (a ratio of Abragam amplitude/Gaussian amplitude); $R_{eg}$ (a ratio of exponential amplitude/Gaussian amplitude); $t_e$ (exponential T2); $t_a$ (Abragam T2); and $t_g$ (Gaussian T2), and their fifteen cross products for a total of twenty variables. The highest existing $Z_k$ (usually Z20) is chosen for the test. A seven sigma limit on the value of the selected $Z_k$ is used, and M-L solutions which result in $Z_k$'s which are outside this range are rejected as M-L fitting failures.

The orthogonal explanatory (Z) variables are used in the regression to determine a model equation 48. Since the z variables are orthogonal, the stepwise technique (or another known technique) is a reliable method for selecting terms for use in the regression model.

The steps shown in FIG. 6A and described herein can be used to form a regression model for each property of interest. For example, a regression model for density, a regression model for xylene solubles, a regression model for MI, a regression model for FRR, and a regression model for MF can be formed via the steps detailed in FIG. 6A.

In accordance with the invention, in order to improve the accuracy of the estimations of a particular property of interest (e.g., MI), two or more regression models for the same property are formed. In a preferred embodiment, a plurality of MI regression models are formed, wherein each MI model is different. Also, according to the invention, a regression model for each discrete variable INBOX is formed. Each INBOX variable corresponds to a different one of the MI regression models. In a preferred embodiment, the accuracy of MI estimations is improved by forming and utilizing two different MI regression models, and INBOX is a two-valued or Boolean variable where one value corresponds to one of the MI regression models and the other value of INBOX corresponds to the other MI model.

Figure 6B:
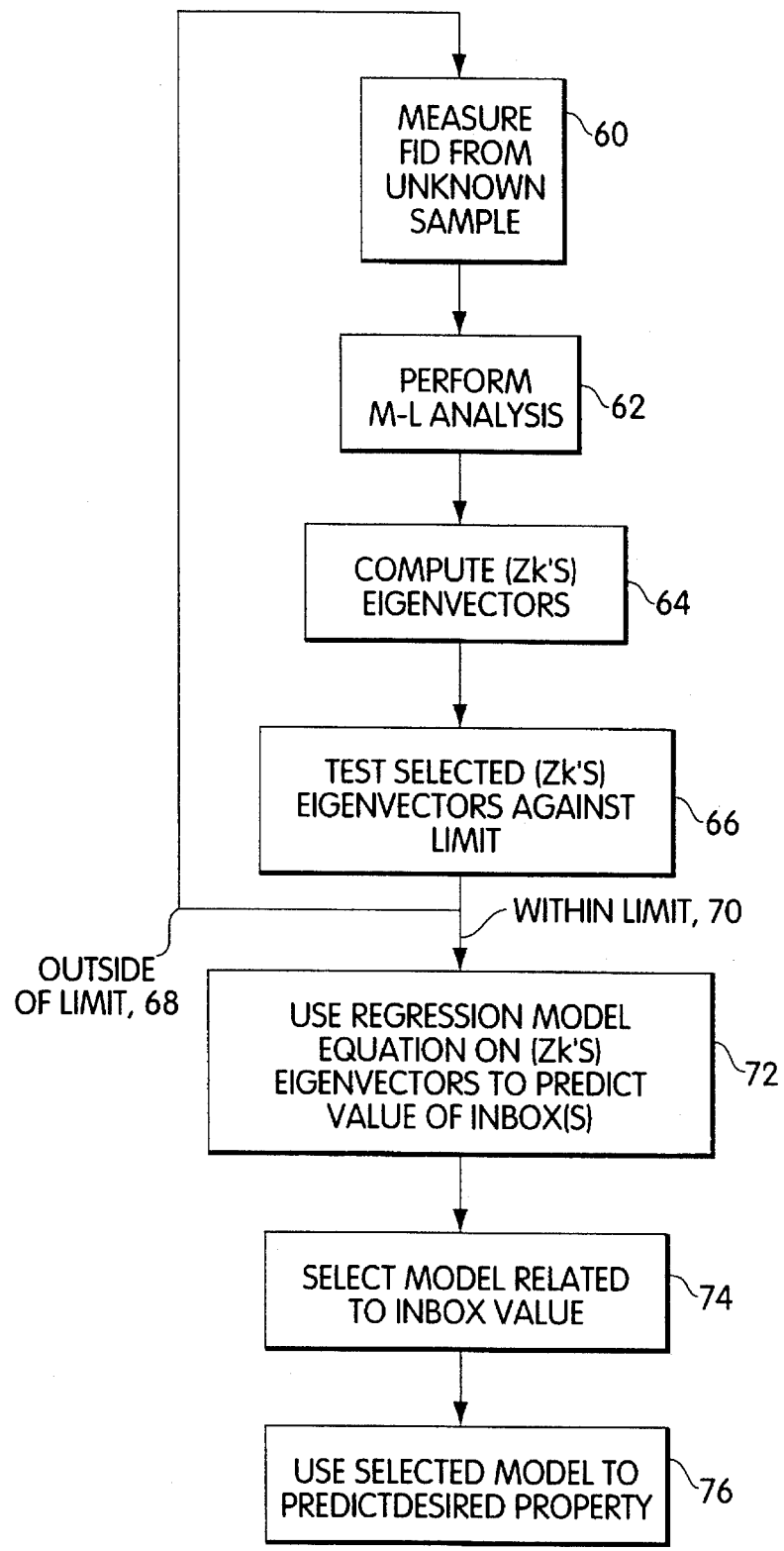

The regression models formed by the steps of FIG. 6A are applied to unknown samples in the manner indicated by the flowchart of FIG. 6B. Referring now to FIG. 6B, the FID of the unknown sample is measured (step 60), and an M-L analysis is performed (step 62) from which the Eigenvectors (i.e., $Z_k$'s) are calculated (step 64). The selected $Z_k$'s (i.e., those with sufficiently small Eigenvalues) are tested against a deviation limitation (step 66) where the determinant of the vector divided by the standard deviation of that vector in the calibration data will cause a rejection of the M-L solution when the result is greater than a particular value. In a preferred embodiment, that value is 7, and in other preferred embodiments, the value is 5 or 9.

In accordance with the invention, the $Z_k$'s for those M-L solutions which pass the limit test (70) are regressed via the model regression equation to predict the value of the discrete variables INBOX (step 72). As described previously, this value corresponds to one of a plurality of regression models for a particular property such as MI. In a preferred embodiment, INBOX is a Boolean variable, and two MI regression models are provided. One value (e.g., 0) of INBOX corresponds to one of the MI models, and the other value (e.g., 1) corresponds to the other MI model. As indicated at step 74, the estimated or predicted value of INBOX is used to select one of the plurality of regression models formed for one of the properties of interest (e.g., to select one of two MI models). With the appropriate MI regression model now identified for this unknown sample, that model is then used to predict an accurate value for MI (step 76). Step 76 involves performing the procedures indicated by steps 62, 64, and 66 in order to predict MI.

Note that if the limit test is failed (68), M-L (step 62) is restarted with different starting assumptions and steps 64 and 66 are repeated. Also, should repeated failures occur with a given unknown sample, that sample is discarded, and a new unknown sample is taken and the steps of FIG. 6B are repeated.

Figure 7:
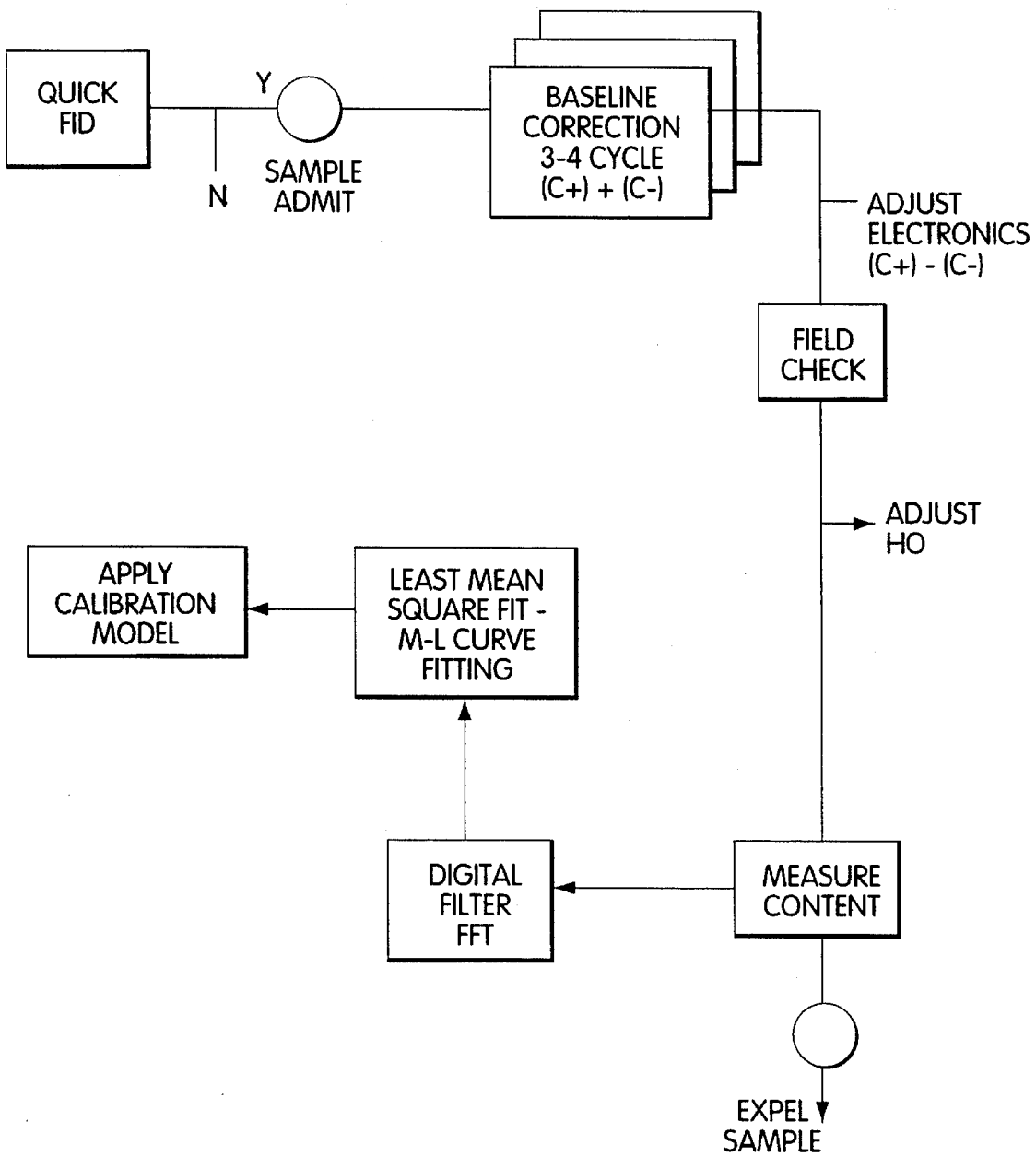
FIG. 7 is a flowchart of the steps to establish an effective industrial measurement.

Referring to FIGS. 1A, 1C, and 7, to establish effective industrial measurements with the NMR system according to the invention, the following procedures are followed. A single FID curve is established to see if the sample area is clear (Quick FID) in an abbreviated cycle of attempting to establish an FID curve. If the sample region is not clear (N), measurement is interrupted to allow valve V2 to open and jets J and gravity to clear the region. A new Quick FID step establishes clearance. Then, a new sample is admitted by closing valve V2, opening valve V1, and making such adjustments of probe P and line L1 as may be necessary to assure sample acquisition. Jets J adjust and stabilize the new sample.

An electronic signal processing apparatus baseline is established in 3 to 4 cycles, each having + and − sub-cycles with the addition of C+ and C− to detect a baseline offset and compensate for it.

Further adjustment is established by coils 124 to adjust H0 (i.e., resonance), and this is enabled by ten to twenty field check cycles of FID curve generation. The C− FID is subtracted from the C+ FID (this process eliminates small baseline offsets) to obtain a workable digitized FID signal which has a maximum value at resonance. H0 is adjusted via coil current generator 117 and coils 124 until such maximum is achieved. In another embodiment, H0 may then be changed to offset the system by a given amount of about 0.1 to 3 KHz.

Then one or more (usually five to one hundred) measurement cycles are conducted to obtain a useable measurement. Each of these five to one hundred cycles involves a modulated transmission/reception/flash A-D conversion and storage of data. The curves are then averaged for M-L curve fitting, and the above-listed intercepts and ratios are established. Similar cycles, often somewhat abbreviated, can be applied for Quick FID, field check, and baseline correction purposes. Each of the sub-cycles (i.e., + and −) of each such cycle involves a capture and utilization of thousands of FID points in data reduction. Each sub-cycle occurs on the order of a second, and the number of such sub-cycles employed depends on the desired smoothing and signal-to-noise ratio (S/N). Generally, S/N improves in a square root relationship to the number of cycles.

As noted in the above-listed related patents and applications, sample tube composition can distort readings. If glass is not used (and it is preferred to avoid glass in industrial usage), the replacement should not be a hydrocarbon plastic. However, fluorocarbons can be effective in several applications since signals from fluorine appear far from resonance. These signals can be distinguished from hydrogen at the levels of sensitivity required and if desired can be filtered or distinguished. In other cases of higher sensitivity measurements (e.g., for gauging relative proportions of amorphous and crystalline species in mixtures thereof), the sample container should be glass or non-protonic ceramic. In some instances, however, fluorocarbon or reinforced fluorocarbon can be used acceptably for polymer measurements. In all such cases, the point is to avoid sample containers with species that can couple with transmitted energy and generate a FID decay curve mimicking the samples.

While particular processing and modeling techniques are described herein, it should be realized by those of ordinary skill in the art that other techniques can be used instead of or in addition to what is described. For example, neural networks and neural network techniques can be used with the NMR system to produce estimations of a variety of properties for a variety of unknown polymer samples.

Variations, modifications, and other implementations of what is described herein will occur to those of ordinary skill in the art without departing from the spirit and the scope of the invention as claimed. Accordingly, the invention is to be defined not by the preceding illustrative description but instead by the following claims.

What is claimed is:

1. A method for measuring polymer properties of samples in real time, comprising:
   storing a plurality of models wherein at least two of the models are useful in predicting a value of a particular property of a sample and at least one of the models is useful in identifying which of the at least two models more accurately predicts the value of the particular property;
   taking a series of samples of an unknown polymer material from an industrial on-line process and placing each of the samples successively in a test region;
   applying a base magnetic field to the sample in the test region to effect precession of nuclei of the sample;
   modifying the precession;
   receiving a resulting relaxation signal representative of a free induction decay of the nuclei of the sample;
   digitizing the free induction decay and analyzing it into component equations;
   processing the component equations with an iterative technique to derive coefficients representative of the component equations;
   utilizing the coefficients, or information based on the coefficients, and the at least one model in order to select one of the at least two models;
   utilizing the coefficients, or information based on the coefficients, and the selected one of the at least two models in order to predict the value of the particular property; and
   discarding the sample from the test region.

2. The method of claim 1 wherein the step of storing the plurality of models comprises storing the at least one model which is useful in predicting a value of a discrete variable having N possible values wherein each of the N possible values corresponds to a different one of the at least two models.

3. The method of claim 2 wherein the step of storing the plurality of models comprises storing the at least two models which are useful in predicting the value of melt index (MI) for the sample.

4. The method of claim 3 wherein the step of storing the plurality of models comprises storing two models which are useful in predicting the value of melt index (MI) for the sample and storing one model which is useful in predicting the value of a Boolean variable having two possible values wherein each of the two possible values corresponds to a different one of the two models.

5. The method of claim 1 wherein the step of taking the series of samples of the unknown polymer material from the industrial on-line process and placing each of the samples successively in the test region comprises taking the series of samples which are samples of polyethylene, polypropylene, or polystyrene.

6. The method of claim 1 wherein the step of storing the plurality of models comprises storing more than two first models which are useful in predicting the value of the particular property of the sample and storing an equal number of second models each of which corresponds to a different one of the first models and which are useful in identifying which one of the first models more accurately predicts the value of the particular property.

7. Apparatus for measuring polymer properties of samples in real time, comprising:

means for storing a plurality of models wherein at least two of the models are useful in predicting a value of a particular property of a sample and at least one of the models is useful in identifying which of the at least two models more accurately predicts the value of the particular property;

means for taking a series of samples of an unknown polymer material from an industrial on-line process and placing each of the samples successively in a test region;

means for applying a base magnetic field to the sample in the test region to effect precession of nuclei of the sample;

means for modifying the precession;

means for receiving a resulting relaxation signal representative of a free induction decay of the nuclei of the sample;

means for digitizing the free induction decay and analyzing it into component equations;

means for processing the component equations with an iterative technique to derive coefficients representative of the component equations;

means for utilizing the coefficients, or information based on the coefficients, and the at least one model in order to select one of the at least two models;

means for utilizing the coefficients, or information based on the coefficients, and the selected one of the at least two models in order to predict the value of the particular property; and means for discarding the sample from the test region.

8. The apparatus of claim 7 wherein the means for storing the plurality of models comprises means for storing the at least one model which is useful in predicting a value of a discrete variable having N possible values wherein each of the N possible values corresponds to a different one of the at least two models.

9. The apparatus of claim 8 wherein the means for storing the plurality of models comprises means for storing the at least two models which are useful in predicting the value of melt index (MI) for the sample.

10. The apparatus of claim 9 wherein the means for storing the plurality of models comprises means for storing two models which are useful in predicting the value of melt index (MI) for the sample and means for storing one model which is useful in predicting the value of a Boolean variable having two possible values wherein each of the two possible values corresponds to a different one of the two models.

11. The apparatus of claim 7 wherein the means for taking the series of samples of the unknown polymer material from the industrial on-line process and placing each of the samples successively in the test region comprises means for taking the series of samples which are samples of polyethylene, polypropylene, or polystyrene.

12. The apparatus of claim 7 wherein the means for storing the plurality of models comprises means for storing more than two first models which are useful in predicting the value of the particular property of the sample and storing an equal number of second models each of which corresponds to a different one of the first models and which are useful in identifying which one of the first models more accurately predicts the value of the particular property.

* * * * *